United States Patent
Louis et al.

(10) Patent No.: US 6,627,662 B2
(45) Date of Patent: Sep. 30, 2003

(54) 3-AMINO-PROPOXYPHENYL DERIVATIVES (I)

(75) Inventors: William John Louis, Rosanna (AU); Graham Paul Jackman, North Clayton (AU); Dimitrios Iakovidis, Doncaster (AU); Simon Nicholas Stewart Louis, Fitzroy North (AU); Olaf Heino Drummer, Sunbury (AU)

(73) Assignee: William John Louis, Austin and Repatriation Medical Centre, Victoria (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,277

(22) PCT Filed: Oct. 10, 1996

(86) PCT No.: PCT/AU96/00638

§ 371 (c)(1),
(2), (4) Date: Sep. 21, 1999

(87) PCT Pub. No.: WO97/13744

PCT Pub. Date: Apr. 17, 1997

(65) Prior Publication Data

US 2003/0100616 A1 May 29, 2003

(51) Int. Cl.$^7$ ............................................. A61K 31/135
(52) U.S. Cl. ........................ 514/652; 514/529; 514/534; 514/651
(58) Field of Search ........................... 558/422; 564/349, 564/351; 514/529, 651, 652, 534; 560/250, 252

(56) References Cited

U.S. PATENT DOCUMENTS

| 4,455,317 A | 6/1984 | Matier |
|---|---|---|
| 4,593,119 A | 6/1986 | Erhardt et al. |
| 4,636,511 A | 1/1987 | Ostermayer et al. |
| 4,810,717 A | 3/1989 | Kam et al. |
| 4,816,604 A | 3/1989 | Louis et al. |
| 4,966,914 A | 10/1990 | Patil et al. |
| 5,013,734 A | 5/1991 | Iguchi et al. |

FOREIGN PATENT DOCUMENTS

| CH | 664 559 | 3/1988 |
|---|---|---|
| DE | 26 49 605 | 5/1977 |
| EP | 004 191 | 9/1979 |

OTHER PUBLICATIONS

Esmolol: A Preliminary Review of its Pharmacodynamic and Pharmacakinetic Properties, and Therapeutic Efficacy, by Benfield et al, Drugs 33:392–412, 1987.

"Development of a Highly Cardioselective Ultra Short–Acting –Blocker, ONO–1101" by Iguchi et al, Chem. Pharm. Bulletin 40(6) 1462–1469, 1992.

*Primary Examiner*—Samuel Barts
(74) *Attorney, Agent, or Firm*—Sughrue Mion, PLLC

(57) ABSTRACT

Compounds of formula (Ia) as potent, $\beta_1$-specific beta blockers with a short duration of action in the systemic circulation, wherein R is 3',4'-dimethoxyphenyl. $R^1$ is hydrogen, and $R^2$ is selected from methyl, ethyl, propyl, isobutyl and isopropyl; or R is 3',4'-dimethoxyphenyl, $R^1$ is selected from fluorine, chlorine and bromine, and $R^2$ is selected from methyl, ethyl, propyl, isopropyl, isobutyl and cyclopropylmethyl; of R is 4'-methoxyphenoxy, $R^1$ is selected from hydrogen, fluorine, chlorine and bromine, and $R^2$ is selected from methyl, ethyl, propyl, isopropyl, isobutyl and cyclopropylmethyl; or R is 3',4'-dimethoxyphenyl, $R_1$ is cyano, and $R^2$ is cyclopropylmethyl; or R is 4'-methoxyphenoxy, $R^1$ is cyano, and $R^2$ is isobutyl; and physiologically acceptable hydrolysable derivatives thereof having the hydroxy group in the 2-position of the 3-aminopropoxy side chain in esterified form, in their racemic and optically active forms, and their pharmaceutically acceptable acid addition salts.

6 Claims, No Drawings

3-AMINO-PROPOXYPHENYL DERIVATIVES (I)

This application is a 371 of PCT/AU96/00638 filed Oct. 10, 1996.

The present invention relates to potent, $\beta_1$-specific beta adrenoreceptor blockers w a short duration of action and to a method for the treatment and/or prophylaxis of conditions for which potent, $\beta_1$-specific beta adrenoreceptor blockers with a short duration of action in the systemic circulation would be particularly advantageous.

The class of drugs known as $\beta$-blockers are well known in the art for treatment of cardiac disorders and particular ophthalmological conditions. However, the optimum combination of properties of such agents depends critically on the condition being treated. Thus, in the long-term treatment of cardiovascular diseases such as hypertension and cardiac arrhythmias, the combination of $\beta_1$-selectivity with high potency, good oral bioavailability and long plasma half-life and duration of action are usually considered optimal, since $\beta_1$-selective compounds have a low incidence of side-effects associated with blockade of $\beta_2$-receptors, such as asthma, and the remaining properties permit treatment by oral administration usually on a once a day basis.

In other conditions where $\beta_1$-selectivity is preferred, some of these properties are not optimal. In ocular administration for the treatment of glaucoma oral availability and long plasma half-life may lead to unwanted systemic side-effects. In the management of cardiac arrhythmias which may arise during induction of anaesthesia or in the care of critically ill patients, short systemic half-life permits rapid control of arrhythmias without the risk of inducing long acting beta blockade. Treatment of glaucoma requires a drug which is well absorbed into the eye. However rapid clearance from the systemic circulation by metabolism to inactive metabolites, after passing through the eye or being swallowed via the naso-lachrymal duct, ensures that treatment is limited to the eye and side-effects are minimised For short-term systemic administration a combination of $\beta_1$-selectivity and short half-life is ideal. For both conditions high potency is required as there is a limit to the practical concentrations which may be formulated into eyedrops, and high potency reduces the dose needed for systemic administration, which tends to be greater for compounds with short half-lives than conventional beta blockers.

Accordingly there is a need to develop $\beta_1$-specific blockers with high potency and a short duration of action in the systemic circulation.

Short acting beta blockers have been described in U.S. Pat. No. 4,966,914, U.S. Pat. No. 4,455,317, U.S. Pat. No. 4,810,717, U.S. Pat. No. 4,593,119, U.S. Pat. No. 5,013,734 and European Patent 041491. All of the short acting beta blocking drugs described in these patents incorporate an easily hydrolysed ester function in their structures.

However, it is difficult to say that the compounds of the above inventions are entirely adequate with regard to the optimum combination of properties required. These may be summarised as (1) adequate blocking effect on the receptor (2) specificity for the $\beta_1$ receptor and (3) a short duration of action in the systemic circulation.

Accordingly there is a need to develop $\beta$-blocking drugs which satisfactorily combine the aforementioned properties (1) to (3).

U.S. Pat. No. 4,816,604 describes the group of compounds of formula (I) as $\beta_1$-selective beta blockers.

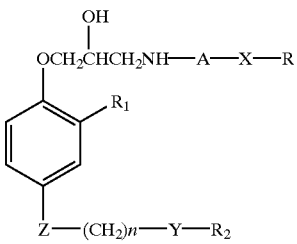

(I)

wherein
R is phenyl or phenyl monosubstituted or independently disubstituted or independently trisubstituted by alkyl of 1 to 4 carbon atoms, alkoxy of 1 to 4 carbon atoms or halogen of atomic number of from 9 to 35, $R_1$ is hydrogen, alkyl of 1 to 4 carbon atoms, alkoxy of 1 to 4 carbon atoms, alklythio of 1 to 4 carbon atoms, cycloalkyl of 3 to 7 carbon atoms, halogen of atomic number of from 9 to 35, trifluoromethyl, 1-pyrrolyl, cyano, carbamoyl, alkenyl of 2 to 5 carbon atoms, alkenyloxy of 3 to 5 carbon atoms wherein the double bond is not attached to the carbon atom adjacent to the oxygen atom, or alkanoyl of 1 to 5 carbon atoms, $R_2$ is alkyl of 1 to 4 carbon atoms, cycloalkyl of 5 to 7 carbon atoms, cycloalkylalkyl of 3 to 7 carbon atoms in the cycloalkyl moiety and of 1 to 4 carbon atoms in the alkyl moiety, phenyl, phenylalkyl of 7 to 10 carbon atoms, or phenyl or phenylalkyl of 7 to 10 carbon atoms monosubstituted or independently disubstituted or independently trisubstituted in the phenyl ring by alkyl of 1 to 4 carbon atoms, alkoxy of 1 to 4 carbon atoms or halogen of atomic number of from 9 to 35.

A is alkylene of 2 to 5 carbon atoms.

X is a bond, an oxygen or a sulfur atom

Y is an oxygen or a sulfur atom, and either Z is an oxygen atom and n is 2 or 3 or Z is a bond and n is 1, 2 or 3, with the provisos, that (a) when $R_2$ is alkyl, then Z is an oxygen atom and the group —NH—A—X—R is other than the moiety of formula

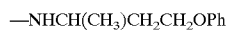

or

(b) when $R_2$ is alkyl and X is a bond or an oxygen atom, then Y is an oxygen atom, and (c) when
$R_2$ is unsubstituted or monosubstituted phenyl,
X is a bond and
Z is an oxygen atom, or
when $R_2$ is cycloalkyl or cycloalkylalkyl and
X is a bond,
then $R_1$ is other than hydrogen, and physiologically acceptable hydrolysable derivatives thereof having the hydroxy group in the 2 position of the 3-aminopropoxy side chain in esterified form, or a pharmaceutically acceptable acid addition salt form thereof.

We have now surprisingly found that a small group of compounds selected from the class generally described in U.S. Pat. No. 4,816,604 have the desirable combination of the aforementioned characteristics (1) to (3). They are particularly active, $\beta_1$-specific and exhibit a short duration of action in the systemic circulation. Such a short duration of action in the systemic circulation is unexpected and could not be predicted as the compounds of the invention are not dependant upon the easily hydrolysed ester groups associated with prior art β-blockers with a short plasma half-life.

Accordingly the present invention provides compounds of formula (Ia) as potent, $\beta_1$-specific beta blockers with a short duration of action in the systemic circulation,

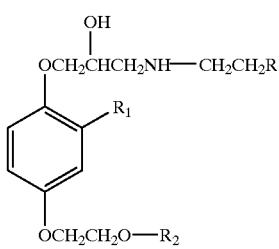

(Ia)

wherein
R is 3',4'-dimethoxyphenyl, $R^1$ is hydrogen, and $R^2$ is selected from methyl, ethyl, propyl, isobutyl and isopropyl; or
R is 3',4'-dimethoxyphenyl, $R^1$ is selected from fluorine, chlorine and bromine, and $R^2$ is selected from methyl, ethyl, propyl, isopropyl, isobutyl and cyclopropylmethyl; or
R is 4'-methoxyphenoxy, $R^1$ is selected from hydrogen, fluorine, chlorine and bromine, and $R^2$ is selected from methyl, ethyl, propyl, isopropyl, isobutyl and cyclopropylmethyl; or
R is 3',4'-dimethoxyphenyl, $R^1$ is cyano, and $R^2$ is cyclopropylmethyl or isobutyl; or
R is 4'-methoxyphenoxy, $R^1$ is cyano, and $R^2$ is isobutyl; and physiologically acceptable hydrolysable derivatives thereof having the hydroxy group in the 2-position of the 3-aminopropoxy side chain in esterified form,
in their racemic and optically active forms, and their pharmaceutically acceptable acid addition salts.

In accordance with a preferred aspect, the present invention provides compounds of formula (Ia) as stated above, wherein
R is 3',4'-dimethoxyphenyl, $R^1$ is hydrogen, and $R^2$ is selected from methyl, ethyl, propyl, isobutyl and isopropyl; or
R is 4'-methoxyphenoxy, $R^1$ is hydrogen and $R^2$ is selected from methyl, ethyl, propyl, isopropyl, isobutyl and cyclopropylmethyl; or
R is 3',4'-dimethoxyphenyl, $R^1$ is cyano, and $R^2$ is cyclopropylmethyl; or
R is 4'-methoxyphenoxy, $R^1$ is cyano, and $R^2$ is isobutyl;
R is 3',4'-dimethoxyphenyl, $R^1$ is bromine, and $R^2$ is methyl;
and physiologically acceptable hydrolysable derivatives thereof having the hydroxy group in the 2-position of the 3-aminopropoxy side chain in esterified form,
in their racemic and optically active forms, and their pharmaceutically acceptable acid addition salts.

In a further aspect of the present invention is provided a method for the treatment and/or prophylaxis of conditions for which potent, $\beta_1$-specific beta blockers with a short duration of action in the systemic circulation would be particularly advantageous which comprises administering to a patient in need of such treatment and/or prophylaxis an effective amount of a compound of formula (Ia).

The present invention also provides the use of a compound of formula (Ia) in the manufacture of a medicament for the treatment and/or prophylaxis of conditions for which potent, $\beta_1$-specific beta blockers with a short duration of action in the systemic circulation would be particularly advantageous.

Preferred compounds, in accordance with the invention are:
1-(4-(2-methoxyethoxy)phenoxy)2-hydroxy-3-(2-(4-methoxyphenoxy)ethylamino)propane;
1-(2-cyano-4-(2-(2-methylpropoxy)ethoxy)phenoxy)2-hydroxy-3-(2-(4-methoxyphenoxy)ethylamino) propane;
S(-)1-(4-(2-ethoxyethoxy)phenoxy)2-hydroxy-3-(2-(3,4-dimethoxyphenyl)ethylamino)propane;
1-(2-cyano-4-(2-cyclopropylmethoxyethoxy)phenoxy)-2-hydroxy-3-(2-(3,4-dimethoxyphenyl)ethylamino) propane; and
1-(4-(2-ethoxyethoxy)phenoxy)-2-hydroxy-3-(2-(3,4-dimethoxyphenyl)ethylamino) propane;
Particularly preferred compounds are
1-(4-(2-ethoxyethoxy)phenoxy)-2-hydroxy-3-(2-(3,4-dimethoxyphenyl)ethylamino) propane and
S(-)1-(4-(2-ethoxyethoxy)phenoxy)2-hydroxy-3-(2-(3,4-dimethoxyphenyl)ethylamino)propane.

Preferred indications for which potent, $\beta_1$-specific beta blockers with a short duration of action in the systemic circulation would be particularly advantageous are ocular treatment of glaucoma, parenteral treatment of cardiac arrhythmias and acute myocardial infarction and parenteral treatment of other cardiac disorders where prolonged blockade of $\beta_1$-adrenoreceptors is undesirable.

Physiologically acceptable hydrolysable derivatives are those derivatives which act as prodrugs and under physiological conditions are cleaved to the corresponding compounds having a hydroxy group in the 2 position of the 3-aminopropoxy side chain.

A group of prodrug derivatives which are esterified forms of the compounds of formula (Ia) are e.g. the compounds of formula (E)

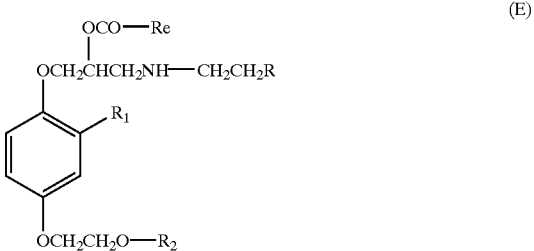

(E)

wherein R, $R_1$ and $R_2$ are as defined above and Re is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently di- or independently trisubstituted in the phenyl ring by halogen of atomic number from 9 to 35, or mono- or independently di- or independently trisubstituted in the phenyl ring by alkoxy of 1 to 4 carbon atoms.

Preferred are the compounds wherein the hydroxy group in the 2 position of the 3-aminopropoxy side chain is in unesterified form.

A compound of the invention may be obtained by a process described in U.S. Pat. No. 4,816,604, comprising reacting a corresponding compound of formula (II),

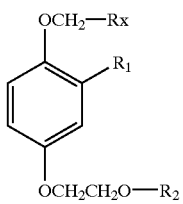
(II)

wherein $R_1$ and $R_2$ are as defined above and Rx is a group capable of reacting with a primary amine to give a 2-amino-1-hydroxyethyl group, with an appropriate compound of formula (III),

(III)

wherein R is as defined above, and, where required, appropriately esterifying the 2 position of the 3-aminopropoxy side chain in the resulting compound of formula (Ia).

The amination process may be effected in a conventional manner for the production of analogous 3-amino-2-hydroxypropoxyaryl compounds. For example, Rx may be a group of formula

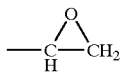

or a derivative of this group, e.g. a group of formula —CH(OH)—CH$_2$L, wherein L is chlorine, bromine or a group Ry-SO$_2$—O—, wherein Ry is phenyl, tolyl or lower alkyl. L is especially chlorine. The reaction is preferably effected in ethanol or in an appropriate ether such as dioxane. Optionally an excess of the amine may be used as solvent. Alternatively, the reaction may be effected in a fusion melt. Suitable reaction temperatures may be from about 20° to about 200° C., conveniently the reflux temperature of the reaction mixture when a solvent is present.

The optional esterification of the 2 hydroxy group in the side chain may be effected in a manner known for the production of analogous esters of 3-amino-2-hydroxypropoxyaryl compounds, if necessary using selective reactions when other reactive groups are present.

Free base forms of the compounds of the invention may be converted into pharmaceutically acceptable acid addition salt forms in a conventional manner and vice versa. Suitable acids for acid addition salt formation include, for example, hydrochloric, hydrobromic, malonic and fumaric acids.

In the compounds of the invention, the carbon atom in the 2 position of the 3-aminopropoxy side chain is asymmetrically substituted. The compounds may thus exist as mixtures of the two optical forms, such as in the racemic form, or in individual optical isomer form. The preferred optical isomer has the S configuration at this asymmetrically substituted carbon atom of the 3-aminopropoxy side chain. Individual optical isomer forms may be obtained in a conventional manner, for example by using optically active starting materials or by fractional crystallisation of racemate salts using optically active acids.

A compound used as a starting material may be obtained in a conventional manner.

In particular, a compound of formula (II) may be obtained by introducing via O-alkylation a group —OCH$_2$—Rx into a compound of formula (IV),

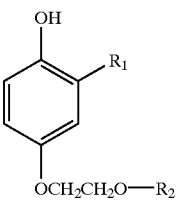
(IV)

wherein $R_1$ and $R_2$ are as defined above. The compound of formula (IV) preferably is reacted in anionic form.

A compound of formula (IV) where $R_1$ is hydrogen may be obtained by selectively etherifying 1,4-dihydroxybenzene at one of the hydroxy groups, e.g. by reaction with a molar equivalent of a compound of formula L—CH$_2$CH$_2$O—R$_2$ wherein R$_2$ and L are as defined above, preferably in an inert solvent such as acetone and in the presence of a base such as potassium carbonate. Alternatively a compound of formula (IV) where $R_1$ is hydrogen may be obtained by deprotecting a corresponding compound of formula V,

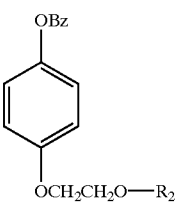
(V)

wherein $R_2$ are as defined above and

Bz is a protecting group, e.g. benzyl or tetrahydropyranyl, under appropriate conditions, e.g. with palladium on charcoal or by acidic hydrolysis.

A compound of formula (V) may e.g. be obtained by appropriately etherifying 4-benzyloxyphenol, e.g. with a derivative L—CH$_2$CH$_2$O—R$_2$, wherein L and R$_2$ are as defined above. L is preferably 4'-toluenesulfonate.

A compound of formula (IV) where $R_1$ is bromine may be obtained by monobromination of the corresponding compound of formula (IV) where $R_1$ is hydrogen. The resulting bromo compound may be converted into a compound of formula (IV) where $R_1$ is cyano by, for example, treatment with cuprous cyanide in dimethyl formamide.

Insofar as the preparation of any particular starting material is not particularly described, this may be effected in conventional manner.

In the following Examples all temperatures are in degrees Centigrade and are uncorrected.

EXAMPLE 1

S(−)-1-(4-(2-Ethoxyethoxy)phenoxy)-2-hydroxy-3-(2-(3,4-dimethoxyphenyl)ethylamino)propane Sodium hydride (9.6 g oil-free) is suspended in anhydrous dimethylformamide (200 ml) and 4-ethoxyethoxyphenol (70.5 g) is added slowly over 30 minutes. The reaction mixture is then cooled to 5° C. and a solution of S(+)-glycidyl-3-nitrobenzenesulfonate (100 g) in dimethylformamide (200 ml) is added over 1 hour. The mixture is allowed to reach room temperature and stirred for a further 1.5 hours. Water is then added slowly to destroy excess sodium hydride, and the mixture diluted with 2 litres of water, and the intermediate epoxide extracted 3 times with 800 ml of ethyl acetate. The extracts are reduced to dryness and redissolved in dioxane (200 ml) and a solution of 3,4-dimethoxyphenylethylamine (70.2 g) in dioxane (200 ml) added. The mixture is heated to reflux for 6 hours, after which the solvent is evaporated and the residue redissolved in diethyl ether. Addition of a saturated solution of hydrogen chloride in diethyl ether (500 ml) cause the hydrochloride salt of the title compound to be precipitated. The product is filtered, dried and recrystallised from isopropanol (750 ml). Yield 103–106 g, m.p. 147–149° C.

4-(2-ethoxyethoxy)phenol is obtained as follows;

2'-Ethoxyethyl 4-toluenesulfonate is prepared by the reaction of 4-toluenesulfonylchloride with 2-ethoxyethanol in the presence of sodium hydroxide. The product is not isolated but allowed to react with 4-benzyloxyphenol and sodium hydroxide, The crude product precipitates on cooling and can be filtered off and washed with 5% sodium hydroxide and water. This material is then suspended in ethanol and debenzylated with hydrogen and 10% palladium on charcoal at atmospheric pressure. The catalyst is removed by filtration on Celite® and the solvent removed under reduced pressure. The residue is dissolved in toluene, filtered and the phenol extra with 5% sodium hydroxide. The extracts are acidified with hydrochloric acid and the phenol extracted into diethylether. After drying the crude phenol can be distilled under reduced pressure to give a colourless liquid, which slowly crystallises, m.p. 39.5–40.5° C.

From the appropriate compounds of formula II, wherein Rx is

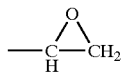

and the appropriate compounds of formula III the following compounds in Table 1 of formula Ia may be obtained in analogous manner to Example 1:

are particularly active, $\beta_1$-specific and exhibit a short duration of action in the systemic circulation. Such a short duration of action in the systemic circulation is unexpected and could not be predicted as the compounds of the invention are not dependant upon the easily hydrolysed ester groups associated with prior art $\beta$-blockers with a short plasma half-life.

The $\beta_1$-specificity and $\beta$-adrenoreceptor blocking potency of the compounds of formula Ia can be demonstrated in vitro by use of isolated tissues of the guinea-pig, in accordance with standard procedures.

Tissue preparation: The animals are killed by a rapid blow to the head followed by cervical dislocation. The chest is opened and the heart and trachea removed and placed in carbonated Krebs-Ringer-Bicarbonate solution (Krebs). Blood is carefully massaged from the chambers of the heart (see L. H. Tung, G. P. Jackman, B. Campbell, S. Louis, D. Iakovidis & W J Louis, *J Cardiovasc. Pharmacol*, 21, (2), 484–488, 1993).

Atria

All extraneous tissue is carefully dissected from the heart, and the atria is dissected from the ventricles. A suture with a loop is tied to each atrium and used to suspend the tissue from an organ bath rod. The other loop is attached to a force transducer loaded with 1 g force. The atria are then maintained in the bath with oxygenated (5% Carbogen) Krebs at 37° C. with changes of Krebs at 10 minute intervals for 50 min. Isoprenaline dose response curves are then measured by addition of isoprenaline in increasing doses from $10^{-11}$ M until a plateau in the response is observed (ca $10^{-5.5}$ M). Doses are increased at two minute intervals and maximum force of contraction and heart rate are recorded. At the end of the dose response curve, the organ bath is flushed with fresh Krebs and washed three times every 10 minutes for 50 minutes. The dose of test drug is then added to the organ bath and allowed to equilibrate for 10 minutes. The isoprenaline does-response curve is then repeated. After washing the atria with Krebs for a further 50 minutes as before, the control does-response curve is repeated in the absence of drug.

Trachea

All extraneous tissue is dissected away and five rings 1–2 mm in width are cut from the trachea and mounted in

TABLE 1

| Example No. | R | $R_1$ | $R_2$ | m.p. ° C. | Configuration at C-2 |
|---|---|---|---|---|---|
| 2 | 4-MeOPhO— | CN | isobutyl | 69–71 | (±) |
| 3 | 3,4-di(MeO)Ph— | Br | Me | 95–96 | (±) |
| 4 | 3,4-di(MeO)Ph— | CN | —CH₂—⊲ | 84–86 | (±) |
| 5 | 4-MeOPhO— | H | Me | 113–115 | (±) |
| 6 | 4-MeOPhO— | H | —CH₂—⊲ | 99–101 | (±) |
| 7 | 3,4-di(MeO)Ph— | H | Et | 140–143 | (±) |

The compounds have more marked and a wider spread of beneficial pharmacological properties than would be expected for compounds having this type of structure. They sequence on loose loops. The rings are suspended from an isometric transducer set at a resting force of 1.0 g. The rings are then incubated in an organ bath at 37° C. in oxygenated (5% Carbogen) Krebs with 3 changes of Krebs every 10 min for 50 min. Carbachol $10^{-6}$ M is then added to the bath to induce a contraction. Once the contractile force is stable, relaxation is induced by addition of increasing doses of isoprenaline ($10^{-8}$ to $10^{-5}$ M) to produce the control dose-response curve. The tissue is then washed in three changes of Krebs every 10 min for 50 min before addition of the drug. After 10 minutes incubation carbachol is added once more and a fresh dose-response to isoprenaline measured. After a further wash of 50 min the control curve is repeated.

The data is used to calculate the $pA_2$ values against atria and trachea (see Mackay, *J. Pharm. Pharmacol.*, 30, 312–313, 1978). These are log values and the higher the value the more potent the compound. The ratio of the values indicates the selectivity of each compound.

The $\beta_1$-specificity of the compounds is indicated in Table 2 below.

TABLE 2

| Compound of | Guinea Pig, pA2 | | |
|---|---|---|---|
| Example No. | Atria, B1 | Trachea, B2 | Selectivity |
| 1 | 7.7 | 4.3 | 2512 |
| 2 | 7.4 | 4.4 | 1000 |
| 3 | 7.1 | 4.2 | 794 |
| 4 | 7.3 | 4.4 | 794 |
| 5 | 7.0 | 4.3 | 501 |
| 6 | 7.2 | 4.1 | 1288 |
| 7 | 7.2 | <4.5 | >501 |

The short duration of action of the compounds of the invention in the systemic circulation was demonstrated in the following experiment.

Healthy male Sprague-Dawley rats were prepared under anaesthesia with indwelling catheters in the carotid artery and jugular vein and allowed to recover for at least 24 h. On the day of the experiment, the arterial catheter was attached to a flexible swivel and then to a pressure transducer for the continuous recording of heart rate and blood pressure. The venous catheters were attached to an infusion pump for drug administration or to a syringe for bolus injections of isoprenaline (0.1 µgt/kg). The catheters were suspended out of the animal's way and the rat was allowed to move freely in a small covered enclosure isolated from outside disturbance. When the BP and HR were stable isoprenaline boluses were given at intervals of 10 minutes until the maximum responses in HR were reproducible (±10%). The doses were repeated for at least 40 minutes and the last 5 readings were considered to constitute the baseline response. The doses were continued at the same interval throughout the test period of a further 150 minutes. Approximately 3.5 minutes before the next dose of isoprenaline the infusion of the test compound was started, to allow for dead volume in the infusion line, and continued for a further 33.5 minutes.

Rats were used for more than one experiment if their catheters remained patent with daily flushing with heparnised saline, but at least 24 hours separated each experiment.

Thus rats with the left carotid artery and left jugular vein cannulated can be studied in the conscious state. This allows continuous recording of heart rate and blood pressure before and after intravenous infusions of beta blocking drugs in selected doses. The duration of beta blockade following cessation of an intravenous infusion of a beta blocking drug can be followed by studying the time taken for the increase in heart rate produced by a standard dose of isoprenaline to return to control values following cessation of the beta blocking drug infusion. The maximum recorded inhibition of the heart rate response to isoprenaline during the infusion of the test drug is estimated, and the pharmacodynamic half-life is the time taken for this inhibition to fall by 50% following the cessation of infusion of the drug.

These studies demonstrate an extremely short half-life of action for the claimed compounds in vivo, in plasma, compared with standard agents such as atenolol and betaxolol which was unexpected and could not have been predicted from the prior art. This property is of great importance in that it allows the safe and controlled use of beta blocking drugs when they are required as short acting intravenous agents in areas of treatment such as anaesthesia and intensive care. This property is also of value in the treatment of disease such as glaucoma as it provides that when the drug is administered by the ocular route any drug which passes into the systemic circulation is rapidly broken down and is therefore much less likely to cause adverse events associated with systemic beta blockade.

The half-life of actions of the compounds in the systemic circulation as determined as described above in vivo in rats is indicated in Table 3.

TABLE 3

| Compound of Example No. | Estimated Plasma Half Life (minutes) |
|---|---|
| 1 | 10–20 |
| 2 | ~17 |
| 3 | ~10 |
| 4 | ~15 |
| 5 | 10–20 |
| 6 | ~10 |
| 7 | ~10 |

It is recognised that when standard beta-blocking drugs are administered by the ocular route some of the drug makes its way into the systemic circulation and can cause adverse systemic effects, including death (U.K Safety of Medicines Report, "Current Problems", No. 28, 1990). Beta-blocking drugs with this level of $\beta_1$ specificity with a short duration of systemic activity would be expected to reduce this risk significantly. The drugs described in the current application are special in that they unexpectedly combine the properties of potency, $\beta_1$-specificity and short half-life in the systemic circulation which provide the basis for a level of safety not previously available for the treatment of glaucoma.

The compounds in free form or in the form of their pharmaceutically acceptable acid addition salts may be administered alone or in suitable dosage forms.

The present invention also provides a pharmaceutical composition comprising a compound of the invention in free base form or in acid addition salt form in association with a pharmaceutical carrier or diluent. Such forms, e.g. a solution, may be produced according to known methods.

When used in the areas of treatment such as anaesthesia and intensive care for the treatment of cardiac disorders, compounds of this invention are advantageously administered parenterally, eg., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. Dosages of about 0.0001 to about 100 mg. per kg. of body weight per hour are generally employed, with preferred dosages ranging from about 0.01 to about 10 mg. per kg. of body weight per hour.

When used for the ocular treatment of glaucoma, the compounds of this invention are advantageously administered topically to the eye in the form of a solution, ointment or solid insert such as is described in U.S. Pat. No. 4,195,085. Formulations may contain the active compound, preferably in the form of a soluble acid addition salt, in amounts ranging from about 0.01 to about 5% by weight, preferably from about 0.2 to about 2% by weight. Unit dosages of the active compound can range from about 0.01 to about 2.0 mg., preferably from about 0.1 to about 0.5 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oil; petroleum jellies; ethyl cellulose; polyvinylpyrrolidone and other conventional carriers. The pharmaceutical preparations may also contain additional components such as emulsifying, preserving, wetting and sterilising agents. These include polyethylene glycol 200, 300, 400 and 600, carbowaxes 1,000, 1,500, 4,000, 6,000 and 10,000, bactericidal components such as quaternary ammonium compounds, phenylmercuric salts known to have cold sterilising properties and which are non-injurious in use, thimerosal, methyl and propyl paraben, benzyl alcohol, phenyl ethanol, buffering ingredients such as sodium chloride, sodium borate, sodium acetate, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose, including conventional phosphate buffer vehicle systems, isotonic boric acid vehicles, isotonic sodium chloride vehicles, isotonic sodium borate vehicles and the like.

The method of treatment of glaucoma of this invention advantageously involves the topical administration of eye drops containing the active compounds. Formulations for eye drops preferably include the active compound as a soluble acid addition salt in a properly buffered, sterile, aqueous isotonic solution.

What is claimed is:

1. A method for the treatment and/or prophylaxis of a subject afflicted with a condition where prolonged blockade of $\beta_1$-adrenoreceptors is undesirable comprising intravenously administering to a subject afflicted with said condition, wherein said condition is selected from the group consisting of cardiac arrhythmia, acute myocardial infarction, and any other cardiac disorder where prolonged blockade of $\beta_1$-adrenoreceptors is undesirable, an effective amount of a racemic or optically active β-blocker represented by formula (Ia) or a pharmaceutically acceptable acid addition salt thereof:

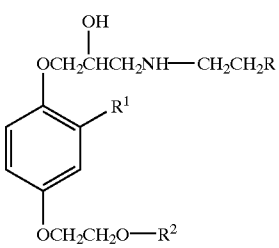

(Ia)

wherein

R is 3',4'-dimethoxyphenyl, $R^1$ is hydrogen, and $R^2$ is selected from the group consisting of ethyl, propyl, isobutyl and isopropyl; or R is 4'-methoxyphenoxy, $R^1$ is hydrogen, and $R^2$ is selected from the group consisting of methyl, ethyl, propyl, isopropyl, isobutyl and cyclopropylmethyl;

or a physiologically acceptable hydrolyzable derivative thereof wherein the hydroxy group in the 2-position of the 3-aminopropoxy side chain is esterified, whereupon said administering, said compound has an in vivo pharmacodynamic half-life of about 20 minutes or less.

2. A method for the treatment and/or prophylaxis of a subject afflicted with a condition where prolonged blockade of $\beta_1$-adrenoreceptors is undesirable comprising intravenously administering to a subject afflicted with said condition an effective amount of a racemic or optically active compound represented by formula (Ia) or a pharmaceutically acceptable acid addition salt thereof:

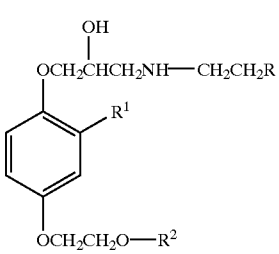

(Ia)

wherein

R is 3',4'-dimethoxyphenyl, $R^1$ is hydrogen, and $R^2$ is selected from the group consisting of ethyl, propyl, isobutyl and isopropyl; or R is 4'-methoxyphenoxy, $R^1$ is hydrogen, and $R^2$ is selected from the group consisting of ethyl, propyl, isopropyl and isobutyl;

or a physiologically acceptable hydrolyzable derivative thereof wherein the hydroxy group in the 2-position of the 3-aminopropoxy side chain is esterified.

3. The method as claimed in claim 2, wherein the conditions are selected from the group consisting of glaucoma, parenteral treatment of cardiac arrhytmias, acute myocardial infarction, and other cardiac disorders where prolonged blockage of $\beta_1$-adrenoreceptors is undesirable.

4. The method of claim 2, wherein

R is 3',4'-dimethoxyphenyl, $R^1$ is hydrogen, and $R^2$ is selected from the group consisting of ethyl, propyl, isobutyl and isopropyl; or a physiologically acceptable hydrolysable derivative thereof wherein the hydroxy group in the 2-position of the 3-aminopropoxy side chain is esterified.

5. The method of claim 2, wherein said compound is S(−)-1-(4-(2-ethoxyethoxy)phenoxy)-2-hydroxy-3-(2-(3,4-dimethoxyphenyl)ethylamino)propane.

6. The method of claim 2 wherein said compound is 1-(4-(2-ethoxyethoxy)phenoxy)-2-hydroxy-3-(2-(3,4-dimethoxyphenyl)ethylamino)propane.

* * * * *